US00PP29914P3

(12) United States Plant Patent
Danziger

(10) Patent No.: US PP29,914 P3
(45) Date of Patent: Nov. 27, 2018

(54) ***PETUNIA* PLANT NAMED 'DLITBIBLIS'**

(50) Latin Name: *Petunia hybrida*
Varietal Denomination: DLITBIBLIS

(71) Applicant: Gavriel Danziger, Beit Dagan (IL)

(72) Inventor: Gavriel Danziger, Beit Dagan (IL)

(73) Assignee: Danziger "DAN" FlowerFarm (IL)

( * ) Notice: Subject to any disclaimer, the term of this patent is extended or adjusted under 35 U.S.C. 154(b) by 0 days.

(21) Appl. No.: 15/530,998

(22) Filed: Apr. 4, 2017

(65) Prior Publication Data

US 2018/0288926 P1 Oct. 4, 2018

(51) Int. Cl.
*A01H 5/02* (2018.01)

(52) U.S. Cl.
USPC ..... Plt./356.13

(58) Field of Classification Search
USPC ..... Plt./356.13, 18, 21, 413
CPC ..... A01H 5/02; A01H 5/00; A01H 5/0255; A01H 6/824
See application file for complete search history.

(56) References Cited

U.S. PATENT DOCUMENTS

PP27,360 P2 * 11/2016 Danziger ..... A01H 5/02 Plt./413
PP28,089 P2 * 6/2017 Danziger ..... A01H 5/02 Plt./413

OTHER PUBLICATIONS

Danziger Littletunia Bicolor Bliss retrieved on Mar. 28, 2018, retrieved from the Internet at https://danzigeronline.com/variety/littletunia-bicolor-bliss/, 4 pp. (Year: 2018).*
Germania Seed Early Bird Catalog 2016, retrieved on Mar. 28, 2018, retrieved from the Internet at http://germaniaseed.com/pdf/2017/2017_plant_EB_WEB.pdf, 3 introductory pages, 5, 68, 194. (Year: 2016).*

* cited by examiner

*Primary Examiner* — June Hwu
(74) *Attorney, Agent, or Firm* — Cassandra Bright

(57) ABSTRACT

A new and distinct *Petunia* cultivar named 'DLITBIBLIS' is disclosed, characterized by a compact, mounded growth habit. The plants are very branched with a medium vigor. The Flower color is purple with white stripes. It is a small size with abundant flowering. The new variety is a *Petunia*, normally produced as an outdoor garden or container plant.

2 Drawing Sheets

Figure 1:
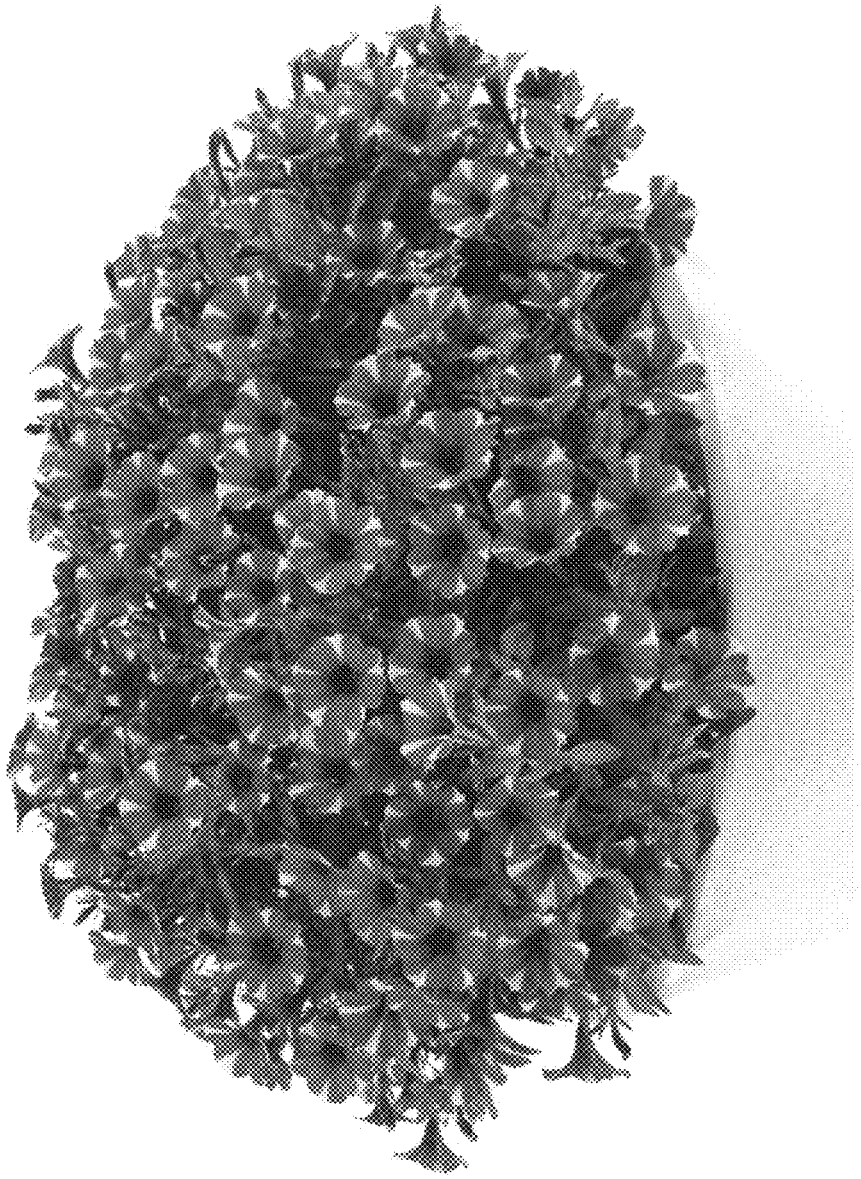

Latin name of the genus and species: *Petunia hybrida.*
Variety denomination: 'DLITBIBLIS'.

BACKGROUND OF THE INVENTION

The new *Petunia hybrida* cultivar is a product of a planned breeding program conducted by the inventor, Gavriel Danziger in Moshav Mishmar Hashiva, Israel. The objective of the breeding program was to produce new *Petunia* varieties with interesting flower color patterns. The cross resulting in this new variety was made during September of 2013.

The seed parent is the unpatented, propriety variety referred to as *Petunia* 'cv. 12-6247'. The pollen parent is the unpatented, propriety variety referred to as *Petunia* 'cv. 12-6263'. The new variety was discovered in July of 2014 by the inventor in a group of seedlings resulting from the 2013 crossing, in a greenhouse in Moshav Mishmar Hashiva, Israel.

Asexual reproduction of the new cultivar 'DLITBIBLIS' was first performed by terminal vegetative cuttings during July of 2014, at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DLITBIBLIS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLITBIBLIS' These characteristics in combination distinguish 'DLITBIBLIS' as a new and distinct *Petunia* cultivar:

1. Compact, mounded growth habit.
2. Very well branched plants with medium vigor.
3. Flowers color is purple with white stripes, forming a heart pattern of purple under some environmental conditions.
4. Flower size is small.
5. Abundant flowering.

PARENT COMPARISON

Plants of the new cultivar 'DLITBIBLIS' are similar to plants of the seed parent, *Petunia* 'cv. 12-3202' in most horticultural characteristics, however, plants of the new cultivar 'DLITBIBLIS' differ in the following;

1. The new variety has a compact, mounded growth habit, the parent variety has an upright growth habit.
2. The parent variety produces less branches and has lower vigor.
3. Flower size of the parent is medium, flower size of the new variety is small.
4. The new variety produces flowers more abundantly.

Plants of the new cultivar 'DLITBIBLIS' are similar to plants of the pollen parent in most horticultural characteristics however, plants of the new cultivar 'DLITBIBLIS' differ in the following;

1. Trailing growth habit.
2. The pollen parent is a more vigorous plant than the new variety.
3. Flower size of the pollen parent is medium, flower size of the new variety is small.
4. Small quantity of flowering, the new variety flowers more abundantly.

COMMERCIAL COMPARISON

Plants of the new cultivar 'DLITBIBLIS' can be compared to the patented commercial variety *Petunia* 'Danlittun3' U.S. Plant Pat. No. 20,054. These varieties are similar in most horticultural characteristics; however, 'DLITBIBLIS' differs in the following:

1. Flower color of the comparator is dark pink, whereas the new variety has purple flowers with white stripes.
2. Flower shape of the comparator is star-shaped, while the flower of the new variety is more rounded.
3. Flower size of the comparator is smaller than the flower of the new variety.

Plants of the new cultivar 'DLITBIBLIS' can also be compared to the unpatented commercial variety *Petunia* 'DANLITT248' U.S. Plant Pat. No. 22,310. These varieties are similar in most horticultural characteristics; however, 'DLITBIBLIS' differs in the following:

1. Comparator flower color is white, the new variety has purple flowers with white stripes.
2. Comparator leaf color is lighter than the leaf color of the new variety.
3. Comparator flower size is smaller than the flower of the new variety.

BRIEF DESCRIPTION OF THE PHOTOGRAPHS

The accompanying photograph in FIG. 1 illustrates in full color a typical plant of 'DLITBIBLIS' grown in a greenhouse, in Moshav Mishmar Hashiva, Israel.

Figure 2:
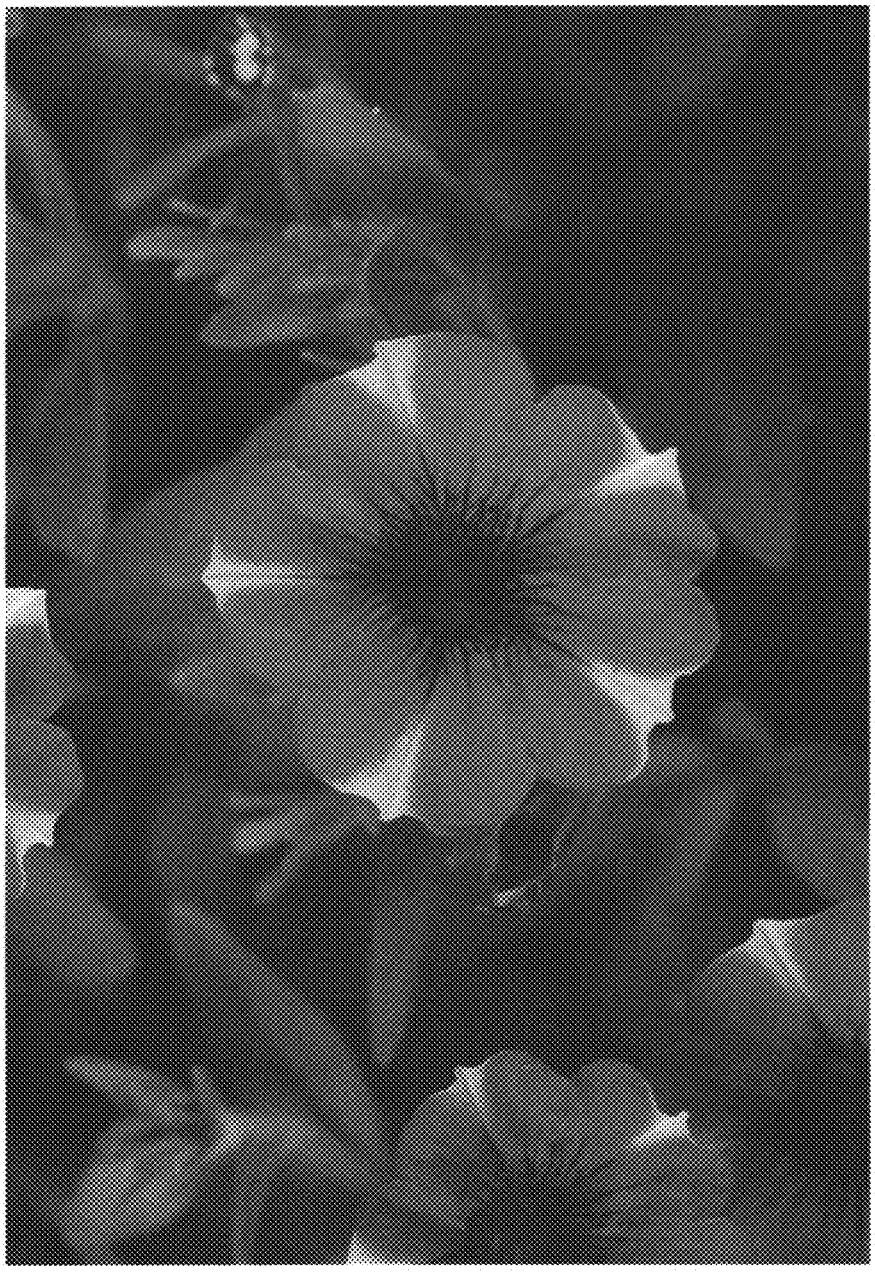

FIG. 2 illustrates in full color a typical mature flower of 'DLITBIBLIS' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DLITBIBLIS' plants grown in greenhouse in Moshav Mishmar Hashiva, Israel, under natural lighting. Measurements were taken during April of 2015. The plants were approximately 60 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia hybrida* 'DLITBIBLIS'.

PROPAGATION

Time to initiate roots: 10-14 days at approximately 20° C.

Root description: Fibrous. Colored tan and white, not accurately measured with R.H.S. chart.

PLANT

Growth habit: Semi-trailing.
Pot size of plant described: 13 cm.
Height: About 15 cm to top of flowering plane.
Plant spread: About 40 cm.
Growth rate: Medium.
Branching characteristics: Very well branched.
Length of primary lateral branches: About 20 cm.
Diameter of lateral branches: About 0.3 cm.
Quantity of primary lateral branches: 8.
Characteristics of primary lateral branches:
- *Form*.—Cylindrical.
- *Diameter*.—About 0.3 cm.
- *Color*.—RHS Yellow-Green 147 B.
- *Texture*.—Pubescent.
- *Strength*.—Good.

Internode length: About 1.0 cm.

FOLIAGE

Leaf:
- *Arrangement*.—Opposite.
- *Quantity*.—Approximately 20 per branch.
- *Average length*.—4.0 cm.
- *Average width*.—2.0 cm.
- *Shape of blade*.—Elliptic.
- *Apex*.—Acute.
- *Base*.—Acute.
- *Margin*.—Entire.
- *Texture of top surface*.—Velvety.
- *Texture of bottom surface*.—Velvety.
- *Color*.—Young foliage upper side: RHS Green 137 A. Young foliage under side: RHS Green 137 C. Mature foliage upper side: RHS Green 137 A. Mature foliage under side: RHS Green 137 C.
- *Venation*.—Type: Pinnate. Venation color upper side: RHS Green 137 B. Venation color under side: RHS Green 137 D.

Petiole:
- *Length*.—About 0.8 cm.
- *Diameter*.—About 0.3 cm.
- *Color*.—RHS Green 137 A.
- *Texture*.—Velvety.

FLOWER

Natural flowering season: Spring, Summer, and Autumn in Mishmar Hashiva, Israel.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3 to 6 days.
Approximate quantity of flowers per plant: About 80.
Persistent or self-cleaning: Self-cleaning.

Bud:
*Shape*.—Tubular.
*Length*.—About 3 cm.
*Diameter*.—About 0.4 cm.
*Color*.—RHS Purple N79 A with 5 stripes yellow-Green 144 C.

Flower size:
*Diameter*.—About 3.5 cm.
*Length*.—About 2.5 cm.
*Flower tube diameter at distal end*.—About 0.7 cm.
*Flower tube diameter at proximal end*.—About 0.2 cm.

Flower:
*Lobing*.—Moderate.
*Upper petal surface flower venation*.—Weakly conspicuous.
*Inner corolla tube venation*.—Strongly conspicuous.
*Flower corolla undulation at side view*.—Weak.

Petals:
*Length from throat*.—About 1.5 cm.
*Width*.—About 1.5 cm.
*Quantity*.—5.
*Texture*.—Velvety.
*Apex*.—Cuspidate.
*Margin*.—Entire.

Color:
*When opening*.—Upper surface: RHS Purple N 79 A. Lower surface: RHS Purple N 79 B.
*Fully opened*.—Upper surface: RHS Red-Purple 71 A with 5 White stripes White NN155 D. White stripes occurring at mid-veins and cuspidate apex. Lower surface: RHS Red-Purple 72 B with 5 White stripes White NN155 C. White stripes occurring at mid-veins and cuspidate apex. Flower throat (inside): RHS Blue 103 A with 5 White stripes White N155A. Flower throat, vein: RHS Violet-Blue 93A. Flower tube (outside): RHS Purple N 79 A with 5 White stripes White N155A. Flower tube, vein: RHS Violet-Blue 94A. The ratio between the 2 colors on the flower (width of stripes) and the pattern created may vary in different growing conditions, light intensity and different seasons. Flowers on the same plant may show less pronunciation of the White stripes, as five shorter triangles around the margins, or even only five White dots around the margins.

Calyx/sepals:
*Quantity per flower*.—5.
*Shape*.—Linear.
*Length*.—About 1.5 cm.
*Width*.—About 0.2 cm.
*Apex*.—Rounded.
*Base*.—Cuneate.
*Margin*.—Entire.
*Texture*.—Velvety.
*Color*.—Upper Surface: RHS Green 137 A. Lower Surface: RHS Green 137 B.

Peduncle: Not present.

Pedicel:
*Length*.—About 1.5 cm.
*Diameter*.—About 0.1 cm.
*Color*.—RHS Yellow-Green 146 B.
*Orientation*.—45 degrees.

Fragrance: None.

REPRODUCTIVE ORGANS

Stamens:
*Number*.—5.
*Filament length*.—About 1.6 cm.

Anthers:
*Length*.—About 0.1 cm.
*Shape*.—Rounded.
*Color*.—RHS White 155 C.
*Pollen*.—Color: RHS Yellow 5 D. Quantity: Abundant.

Pistil:
*Number*.—1.
*Length*.—About 2.0 cm.
*Style*.—Length: About 1.4 cm. Color: RHS Yellow-Green 144 C.
*Stigma*.—Shape: Rounded. Color: RHS Yellow-Green 144 B. Ovary Color: RHS Yellow-Green 144 A.

OTHER CHARACTERISTICS

Seeds and fruits: About 50 Brown, rounded seeds of about 0.5 mm diameter, per one brown, conical capsule.

Disease/pest resistance: Neither resistance nor susceptibility to the normal diseases and pests of *Petunia* have been observed. Typical well known diseases include: *Botrytis cineria, Fusarium, Pythium, Phytophthora,* and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DLITBIBLIS' as herein illustrated and described.

* * * * *